(12) United States Patent
Gillis et al.

(10) Patent No.: US 6,506,949 B2
(45) Date of Patent: Jan. 14, 2003

(54) PROCESS FOR RING NITRATING AROMATIC COMPOUNDS IN A TUBULAR REACTOR HAVING STATIC MIXING ELEMENTS SEPARATED BY COALESCING ZONES

(75) Inventors: Paul A. Gillis, Lake Jackson, TX (US); Helge Braun, Lake Jackson, TX (US); Joerg Schmidt, Halle/Saale (DE); Jan Willem Verwijs, Hoek (NL); Harald Velten, Bahia (BR); Kristina Platkowski, Boehlitz-Ehrenberg (DE)

(73) Assignee: Dow Global Technologies, Inc., Midland, MI (US)

( * ) Notice: Subject to any disclaimer, the term of this patent is extended or adjusted under 35 U.S.C. 154(b) by 0 days.

(21) Appl. No.: 09/797,256

(22) Filed: Mar. 1, 2001

(65) Prior Publication Data

US 2001/0043894 A1 Nov. 22, 2001

Related U.S. Application Data

(60) Provisional application No. 60/186,522, filed on Mar. 2, 2000.

(51) Int. Cl.$^7$ .............................................. C07C 205/00
(52) U.S. Cl. ....................... 568/939; 568/932; 568/927
(58) Field of Search ............................... 568/939, 932, 568/927

(56) References Cited

U.S. PATENT DOCUMENTS

| | | | | |
|---|---|---|---|---|
| 2,256,999 | A | 9/1941 | Castner | 260/645 |
| 3,431,312 | A | 3/1969 | Toischer et al. | 260/645 |
| 3,664,638 | A | 5/1972 | Grout et al. | 259/4 |
| 4,021,498 | A | 5/1977 | Alexanderson et al. | 260/645 |
| 4,091,042 | A | 5/1978 | Alexanderson et al. | 260/645 |
| 4,973,770 | A | 11/1990 | Evans | 568/929 |
| 5,313,009 | A | 5/1994 | Guenkel et al. | 568/927 |
| 5,616,818 | A * | 4/1997 | Pirkl et al. | 568/932 |
| 5,763,687 | A | 6/1998 | Morisaki et al. | 568/927 |
| 5,763,697 | A | 6/1998 | Hermann et al. | 568/939 |
| 5,963,878 | A | 10/1999 | Brereton et al. | 568/927 |

FOREIGN PATENT DOCUMENTS

| | | |
|---|---|---|
| EP | 0 489 211 A1 | 6/1992 |
| EP | 0 668 263 A1 | 1/1995 |
| EP | 0 779 270 A1 | 12/1996 |

* cited by examiner

*Primary Examiner*—Jafar Parsa

(57) ABSTRACT

A tubular reactor characterized by having short static mixing elements separated by coalescing zones is used to conduct multiphase liquid/liquid reactions. Small droplets of one of the phases are dispersed into the other phase by the static mixing elements. These droplets coalesce and at least partially phase separate as the mixture passes through the subsequent coalescing zone. The tubular reactor is particularly suitable for nitrating organic compounds while forming low levels of improperly nitrated by-products and low levels of nitrophenolics.

14 Claims, 1 Drawing Sheet

PROCESS FOR RING NITRATING AROMATIC COMPOUNDS IN A TUBULAR REACTOR HAVING STATIC MIXING ELEMENTS SEPARATED BY COALESCING ZONES

This application claims the benefit of U.S. Provisional Application No. 60/186,522, filed on Mar. 2, 2000.

BACKGROUND OF THE INVENTION

This invention relates to a tubular reactor, and for processes of conducting liquid/liquid multiphase reactions, particularly nitrations of aromatic compounds, in tubular reactors.

Reactions between immiscible or only slightly miscible liquids are commonly performed. Typical such reactions include an aqueous phase that is reacted with an immiscible organic phase. Because the desired chemical reactions usually occur mainly at the interface of the liquid phases, an important factor in obtaining a complete reaction or a commercially acceptable rate of reaction is to intensely mix the phases. There are various ways of accomplishing this. A common way is to conduct the reaction with mechanical mixing, such as by using an agitator blade. Cascade reactors are also known. Apparatus of these types have various shortcomings. Moving parts tend to wear out and need maintenance or replacement. Usually the apparatus is relatively expensive. Often, back-mixing occurs, leading to the formation of undesired byproducts or in some cases, over-reaction of the raw materials.

The problems associated with reactions between immiscible liquids are illustrated well by the nitration of aromatic compounds. Two commercially important nitrated aromatic compounds are mononitrobenzene (MNB) and dinitrotoluene, which are prepared by nitrating benzene and toluene, respectively. MNB is a common solvent and can be converted to another commercially important compound, aniline. Similarly, nitrated toluene products such as dinitrotoluene are used to make derivatives such as toluene diamine, which can be further converted to toluene diisocyanate, an important raw material for making polyurethane polymers.

Aromatic ring nitration reactions are ordinarily conducted by mixing the aromatic compound with nitric acid in the presence of sulfuric acid. An adiabatic process for producing mononitrobenzene is described in U.S. Pat. No. 2,256,999 to Castner. In Castner's process, as in all similar benzene nitration processes, the acids form a phase that is immiscible with the aromatic compound. Consequently, Castner describes using a series of agitated tanks for conducting the reaction in order to obtain a commercially acceptable reaction rate. However, the Castner process suffers from several difficulties, primarily low yields and the formation of high levels of nitrophenolic impurities. In addition, the Castner process forms undesirably high levels of overnitrated products, primarily dinitrobenzene.

The reliance on high shear mixing to deal with immiscible raw materials is reflected in other nitration processes as well. In U.S. Pat. Nos. 4,021,498 and 4,091,042, Alexanderson et al. describe using a "vigorously agitated" tubular reactor to conduct the reaction. This alone was not sufficient to satisfactorily produce the desired product, however. Consequently, Alexanderson et al. require careful selection of the proportions of starting materials in order to reduce the level of impurities in the product. This general approach to reducing impurities was continued in U.S. Pat. No. 5,313,009 to Guenkel et al., in which impurity formation is said to be reduced using a specially designed mixer, which produces extremely fine benzene bubbles in the acid phase, followed by a tubular reactor that may include additional static mixing elements. Like Alexanderson et al., Guenkel et al. found that very specific proportions of starting materials were necessary in order to obtain a product with low levels of impurities.

Other references are similar. In U.S. Pat. No. 3,431,312 to Engelbert et al., nitration is performed in a series of cascade reactors, all of which are equipped with mixers or stirrers. In U.S. Pat. No. 4,973,770 to Evans, the reaction is performed by forming a turbulent jet of nitric and sulfuric acid to produce droplets of mixed acid having a size of from less than 1 $\mu$m to about 10 $\mu$m in diameter and contacting the acid droplets with the nitratable organic compound. In U.S. Pat. No. 5,963,878, a pipe nitrator discharges into a stirred tank type reactor.

In the process described in U.S. Pat. No. 5,763,687 to Morisaki, the reaction is conducted in a tube or pipe reactor equipped with a number of specially designed static mixing elements.

Thus, nitrations of aromatic compounds typify many of the problems that attend multiphase liquid/liquid reactions. On the one hand, for economic reasons it is necessary to obtain an acceptable reaction rate, and this is usually facilitated by increasing the contact between the phases. On the other hand, over-contacting the phases can cause impurities, particularly nitrophenols and cresols to form. Similarly, back-mixing or over-contacting the phases may cause even the desired reaction to go too far. With nitration reactions, this is seen in the production of over-nitrated products such as dinitrobenzene (in MNB production). The formation of impurities in this manner reduces yield, thereby reducing the overall economic efficiency of the process.

Thus, it would be desirable to provide an apparatus with which multiphase liquid/liquid reactions can be conducted, which provides good control of the reaction and efficient mixing of the phases. It would also be desirable to provide a process for conducting multiphase liquid/liquid reactions efficiently, with good yields and low levels of impurities and byproducts being formed. In particular, it would be desirable to provide a method of nitrating aromatic compounds with good yields, low levels of nitrophenolic impurities and low levels of undesired by-products, using relatively inexpensive equipment.

SUMMARY OF THE INVENTION

In one aspect, this invention is a tubular reactor comprising a tube having an inlet end into which a reaction mixture enters the tubular reactor, an outlet end from which a product stream emerges, and, located in said tube between said inlet and outlet ends, a sequence of short static mixing elements separated by coalescing zones, wherein (a) the length of each static mixing element is no greater than about 6 times the diameter of that static mixing element, and (b) the length of each of said coalescing zones is at least about 4 times the diameter of that coalescing zone.

The tubular reactor of the first aspect provides a simple apparatus in which multiphase liquid/liquid reactions can be conducted with good yields and low levels of impurities and by-products.

In a second aspect, this invention is a process for conducting a multiphase liquid/liquid reaction, comprising (1) introducing a stream of a multiphase liquid reaction mixture into an inlet end of a tubular reactor having a sequence of short static mixing elements separated by coalescing zones, wherein (a) the length of each coalescing zone is selected together with a flow rate of the reaction mixture such that as said reaction mixture passes through said coalescing zone, droplets of at least one liquid phase of the multiphase reaction mixture coalesce and at least partially phase separate from at least one other liquid phase of said reaction mixture, forming a topmost portion of said reaction mixture rich in one phase and a bottommost portion of said reaction mixture poor in said one phase, and when said reaction mixture passes from a coalescing zone through a static mixer element, said topmost and bottommost portions of said reaction mixture are sheared and blended to redisperse the coalesced droplets as smaller droplets in said at least one other liquid phase, (2) passing said reaction mixture under reaction conditions through said tubular reactor, and (3) withdrawing a stream containing a desired reaction product from an outlet end of the tubular reactor.

In a third aspect, this invention is a process for nitrating an aromatic compound, comprising passing under reaction conditions a reaction mixture including an aromatic compound and an acid phase containing sulfuric or phosphoric acid, nitric acid and water through a tubular reactor having a sequence of short static mixing elements separated by coalescing zones, wherein (a) the length of each of said coalescing zones is selected together with a flow rate of the reaction mixture such that as said reaction mixture passes through a coalescing zone, droplets of the aromatic compound coalesce and at least partially phase separate from said acid phase, forming a topmost portion of said reaction mixture rich in the organic compound and a bottommost portion of said reaction mixture poor in the organic compound, and when said reaction mixture passes from a coalescing zone through a static mixer element, said topmost and bottommost portions are sheared and blended to redisperse the aromatic compound as small droplets in the acid phase.

This process gives excellent yields of the desired nitration product, with low levels of under- and overnitrated products and nitrophenol impurities. In addition, low pressure drops in the tubular reactor allow the use of smaller pumping equipment, thereby reducing capital costs and energy consumption.

DESCRIPTION OF THE PREFERRED EMBODIMENTS

The tubular reactor of the invention is a tube or pipe having an inlet end and an outlet end. Within the tube are a series of intermittently spaced, short static mixing elements separated by coalescing zones. By "coalescing zone", it is meant a region of the tubular reactor in which mixture blending is minimal. The coalescing zone is designed so that as the reaction mixture travels through it, gravimetric forces are predominate over hydrodynamic forces, so droplets of the dispersed liquid phase coalesce and at least partially phase separate.

The static mixing elements shear and blend these portions so that the disperse phase droplets are formed into smaller droplets dispersed in at least one other phase. The mixed reaction mixture then flows through a subsequent coalescing zone, and the process of droplet coalescence and phase separation repeats. In this way, the reaction mixture goes through a series of mixing and coalescing processes until the reaction is substantially complete.

Short length static mixing elements are used, so that the residence time of the reaction mixture in each of the static mixing elements does not significantly exceed that required to provide the required shearing and blending of the reaction mixture. The length of the static mixing can be expressed in terms of length/diameter ratio, or in terms of residence time. Of course, residence time is dependent on flow rates. The static mixing units suitably have a length/diameter ratio of no greater than about 6, preferably no greater than about 2, more preferably no greater than about 1, even more preferably no greater than about 0.5, most preferably no greater than about 0.2. In terms of residence times, the length of the static mixing elements is selected together with operating flow rates such that the residence time of the reaction mixture in each static mixing element is no greater than about 2 seconds, preferably no greater than about 1 second, more preferably no greater than about 0.25 second, most preferably no greater than about 0.1 second.

The selection of the design of the static mixing elements is not critical provided the required shearing and blending is achieved. Thus, the static mixing elements can include pins, baffles, tabular inserts, including twisted tabular inserts of the type described in U.S. Pat. No. 5,763,687, and the like. However, designs that minimize the pressure drop across the static mixing element are preferred. Preferably, the pressure drop across each static mixing element is no greater than about 1.0 bar, more preferably no greater than about 0.7 bar, most preferably no greater than about 0.4 bar, at the flow rates used in the process.

Figures 2, 3:
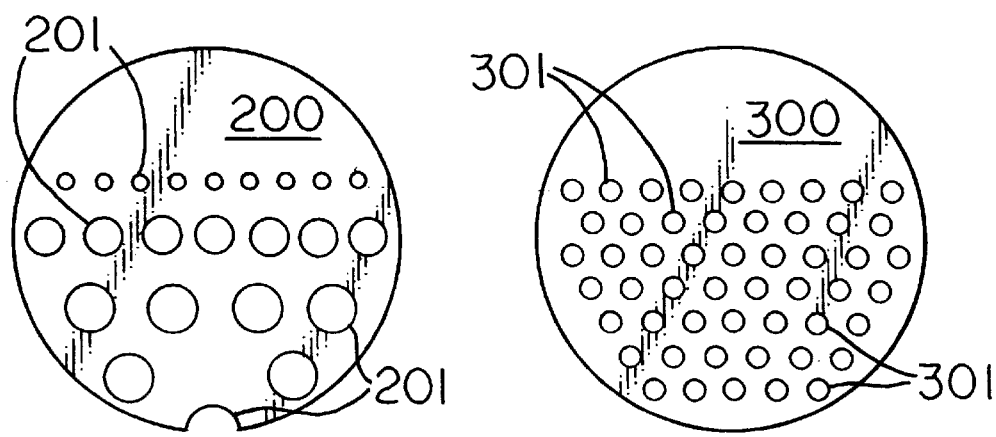
FIGS. 2 and 3 are front views of two embodiments of perforated plates that are preferred static mixing units for use in the tubular reactor of the invention.

A preferred static mixing element is a plate situated approximately perpendicularly to the direction of flow, which has perforations in only a portion of its surface. Generally, the unperforated section of the plate will reside primarily near the top or the bottom of the plate, as the plate is oriented in the tubular reactor. The perforations are more preferably situated on only the topmost or bottommost ½ to ⅔ of the plate. Two suitable designs for such perforated plates appear in FIGS. 2 and 3. In FIG. 2, plate 200 has a plurality of holes 201 located in the bottommost ⅔ of the plate. The diameter of holes 201 increase towards the bottom of the plate. In FIG. 3, plate 300 has holes 301 of uniform diameter situated in the bottom ⅔ of the plate. Plates 200 and 300 are shown in the orientation in which they would most preferably be installed, with the non-perforated portions of plates 200 and 300 located at the top. However, in some circumstances it may be more suitable to install plates 200 or 300 with the non-perforated portions near the bottom. An example of this is an instance where the high density liquid phase is also the low volume phase in the reaction mixture. The plates preferably have a least one perforation near the bottom, in order to facilitate draining the tubular reactor.

Preferred plate mixers are conveniently installed at flanges between adjoining sections of the tubular reactor. Alternatively, they can be installed as inserts within the reactor.

The individual static mixing elements are separated by coalescing zones within the tubular reactor. The coalescing zones are generally oriented so that a degree of gravimetric phase separation occurs in the reaction mixture as it travels from one static mixing element to the next. Thus, as the reaction mixture moves through a coalescing zone and approaches the next static mixing element, it separates into a topmost portion that is relatively rich in a lower density component of the reaction mixture, and a bottommost portion that is relatively poor in the lower density component. The coalescing zones will typically contain substantially no mixing elements.

The length of the coalescing zones can be expressed in terms of length/diameter ratio or in terms of residence times. Again, residence times will depend on flow rates. In designing a tubular reactor for a particular process, various factors such as design flow rates, viscosities of the reactants, the rate at which the phases will separate under the conditions in the reactor, among others, will all affect the length of the coalescing zones. In general, the length of each coalescing zone is selected together with design operating flow rates so that as the reaction mixture travels through a particular coalescing zone, the dispersed phase has time to coalesce and at least partially phase separate from the other phase before reaching the next static mixing element.

In order to accomplish the desired separation of the phases, the coalescing zones suitably have a length/diameter ratio of at least about 4, preferably at least about 6, more preferably at least about 9, even more preferably at least about 15, up to 1000 or more, preferably up to about 200, more preferably up to about 120. In terms of residence times, the length of the coalescing zones is suitably chosen such that the residence time of the reaction mixture in the coalescing zone is from about 1 second, preferably from about 2, more preferably about 3 seconds, to about 100 seconds, preferably about 50 seconds, more preferably about 30 seconds.

In many reaction systems, products (or byproducts or impurities) form that may tend to compatibilize the separate liquid phases somewhat. Consequently, the time needed for phase separation may increase as the reaction mixture progresses through the tubular reactor. To accommodate this condition, a preferred variation of the tubular reactor is one in which the length of the coalescing zones increases towards the outlet end of the reactor. In this way, the reaction mixture resides longer in the coalescing zones towards the outlet end of the reactor, thus allowing more time for the mixture to phase separate. This lengthening can be continuous throughout the reactor, so that each succeeding coalescing zone is longer than the one before. Alternatively, groups of coalescing zones with a shorter length can be followed by one or more coalescing zones having longer lengths, and so forth, thereby increasing the lengths of the coalescing zones in a step-wise fashion.

Conversely, in some reaction systems, phase separation may increase as the reaction mixture progresses through the tubular reactor. In such a case, the coalescing zones may become increasingly shorter toward the outlet end of the reactor.

In any event, it is unnecessary for any coalescing zone to extend past the point where this coalescence and phase separation has completed. As soon as this phase separation has occurred, the reaction mixture can be passed through another static mixing element as before.

As gravimetric phase separation occurs in the coalescing zones, the orientation of the coalescing zones in space is chosen to facilitate that separation. Usually, this means that the coalescing zones will be oriented generally horizontally. However, the coalescing zones may also include risers and down legs, as shown at numerals 30 and 31 in FIG. 1, so the reactor accommodates the geometry of the surrounding structure.

The tubular reactor may consist of a series of short segments, that are joined together, such as by flanges, to form the overall reactor. In addition, the tubular reactor may be adapted to handle adiabatic reactions, as well as exothermic or endothermic reactions that require heat and/or cooling to be applied. Heat and cooling are conveniently applied using well-known techniques, such as jackets, heat exchangers or other means for applying or removing heat.

Figure 1:
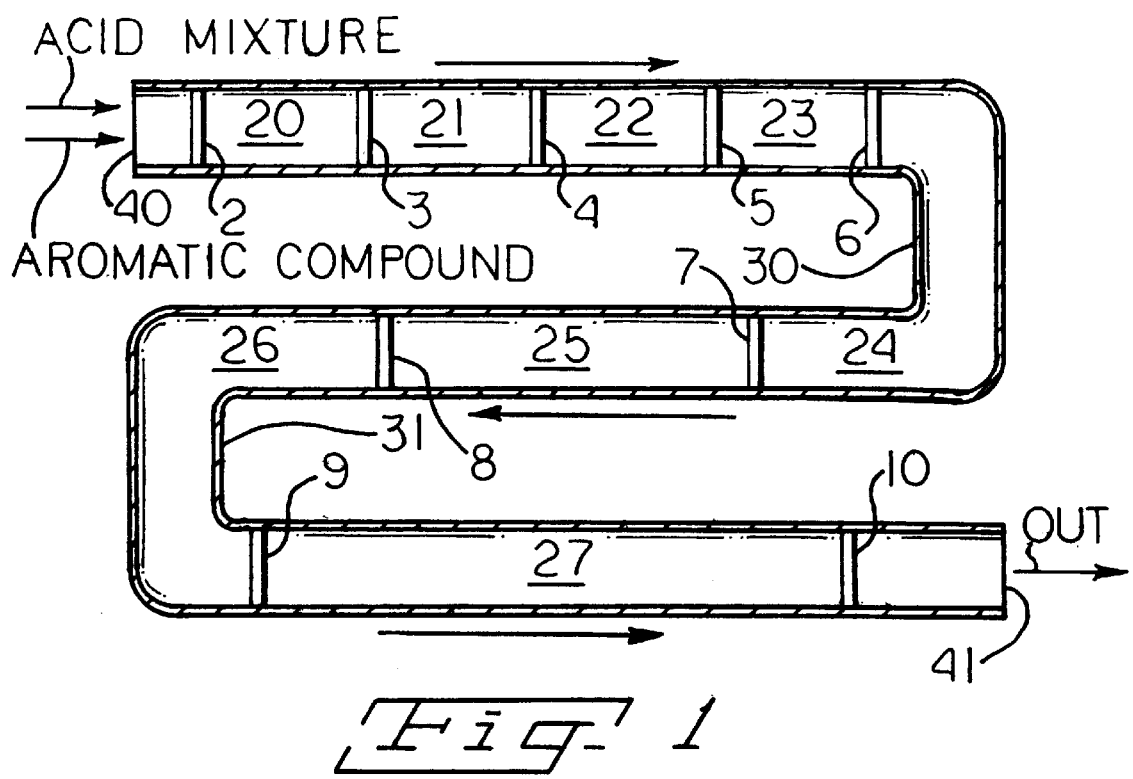
FIG. 1 is a cross-sectional side view (not to scale) of an embodiment of a tubular reactor of the invention.

FIG. 1 illustrates a suitable tubular reactor. Tubular reactor 1 includes an inlet end 40 at which the reaction mixture is fed into the reactor, and an outlet end 41 from which a product stream 13 emerges. It is not necessary to pre-mix the reactants before these materials enter the tubular reactor. The direction of flow is indicated by arrows. Tubular reactor 1 includes sequential static mixing sections 2, 3, 4, 5, 6, 7, 8, 9 and 10, which are separated by sequential coalescing zones 20, 21, 22, 23, 24, 25, 26 and 27. As shown in FIG. 1, the first three coalescing zones, zones 20, 21 and 22, are of approximately equal length. In the preferred embodiment shown in FIG. 1, each succeeding coalescing zone 23, 24, 25, 26 and 27 is longer than the one before, thus providing a longer residence time in each succeeding coalescing zone 23, 24, 25, 26 and 27.

The overall length of the tubular reactor preferably is chosen together with design flow rates so that the reaction is essentially completed in the reactor. Generally, a residence time of about 10 seconds, preferably about 30 seconds, more preferably about 50 seconds to about 200 seconds, preferably about 150 seconds, more preferably about 80 seconds is adequate. At typical commercial flow rates of about 0.25 to about 5 meters/second, a suitable length for the tubular reactor is from about 2.5 meters, preferably from about 10 meters, more preferably from about 25 meters, to about 800 meters, preferably about 300 meters, more preferably about 150 meters.

If appropriate for a particular reaction system, the reaction mixture may discharge from the tubular reactor into a separate reaction vessel in which the reaction is completed.

Suitable diameters for the tubular reactor range from about 2.5 cm, preferably about 10 cm, more preferably 15 cm, to about 50 cm, preferably about 40 cm, more preferably about 25 cm.

The tubular reactor of the invention contains at least two static mixing elements, each (except optionally the last) followed by a coalescing zone. Preferably the tubular reactor contains at least 5, more preferably at least 7, even more preferably at least 10 static mixing elements, each (except optionally the last) followed by a coalescing zone. The maximum number of static mixing elements depends on the particular chemical reaction being conducted, and in principal there is no maximum on the number of static mixing elements that may be present. However, most reactions can be operated efficiently and economically with up to about 50 static mixing elements, preferably up to about 25, more preferably up to about 15.

Multiphase liquid/liquid reactions are conducted in the tubular reactor of the invention by feeding the reaction mixture through the reactor at an appropriate flow rate. An appropriate flow rate is one sufficient to create the requisite shearing and blending of the dispersed phase into small droplets as the reaction mixture passes through the static mixing elements, yet provides sufficient residence time in the coalescing zones for the droplets to coalesce and at least partially phase separate as described before. Although appropriate flow rates may vary considerably based on many factors, a flow rate of from about 0.25 m/s, preferably about 0.5 m/s, to about 5 m/s, preferably to about 3 m/s, more preferably to about 1.5 m/s, is suitable for a broad range of reactions.

Plug-flow conditions are preferred. As the reaction mixture passes through the tubular reactor, it reaches the outlet end of the reactor and is withdrawn. Recovery of the desired product, purification (if needed) and recycling of any process streams may be performed as appropriate for the particular process.

As the tubular reactor of the invention is adapted for handling multiphase liquid reaction mixtures, the reaction mixture will preferably contain at least two partially immiscible phases. The phases preferably have somewhat different densities, such as a difference of at least 0.01 g/cc, more preferably at least about 0.03 g/cc, even more preferably at least 0.05 g/cc, in order to facilitate gravimetric separation of the phases in the coalescing zones. Typically, with appropriate mixing one of the phases (usually the low volume phase) will become dispersed as droplets in the other.

The tubular reactor of the invention is particularly suitable for nitrating various aromatic compounds and for conducting mono- and/or dinitrations. Thus, suitable aromatic compounds include benzene, toluene, monochlorobenzene and the like. The process is especially suitable for the mononitration of benzene.

In these reactions, the reaction mixture comprises the aromatic compound to be nitrated, sulfuric acid, nitric acid and water. Nitric acid may be present entirely or in part in the form of nitronium ion ($NO_2^+$), but for the purposes of this document will always be referred to by the shorthand "nitric acid", regardless of the actual form. For mononitration reactions, the aromatic compound typically will be present in a slight stoichiometric excess over the nitric acid. Preferred molar ratios of aromatic compound to nitric acid are about 1.0 to about 1.5:1, more preferably 1.05 to about 1.3:1, most preferably about 1.05 to about 1.15:1, for mononitration. For dinitration reactions, the nitric acid is typically in excess. Preferred molar ratios of aromatic compound to nitric acid in dinitration reactions are about 0.4 to about 0.75:1, more preferably about 0.4 to about 0.55:1, most preferably about 0.42 to about 0.48:1.

The concentration of nitric acid in the acid mixture is advantageously from about 1% by weight, preferably about 2.5% by weight, more preferably 4% by weight, to about 8% by weight, preferably 6% by weight, more preferably about 4.5% by weight. The sulfuric acid concentration in the acid mixture is advantageously about 50%, preferably about 60%, more preferably about 62% to about 75%, preferably about 68%. The water content in the acid mixture is advantageously from about 20%, preferably from about 25%, more preferably from about 28% to about 40%, preferably to about 35%.

In conducting the process, the acids, water and aromatic compound are introduced to the tubular reactor at the correct relative proportions, and in amounts sufficient to give the desired flow rates. The acids and water may be premixed, or may be introduced into the tubular reaction separately. If desired, the acids and aromatic compound may be mixed beforehand. Flow rates are sufficient to provide adequate shearing and blending across the static mixers to disperse the aromatic compound as small droplets in the acid phase. The raw materials are advantageously heated to a temperature of about 50 to about 120° C., preferably about 60–100° C., before the acids and aromatic compound are mixed. The reactor is advantageously pressurized to avoid flashing the aromatic compound. Plug-flow is maintained in the reactor in order to minimize back mixing at the static mixing elements. Back mixing is believed to contribute to the formation of impurities such as nitrophenols and cresols.

The nitration reaction is exothermic, and the tubular reactor may be cooled if desired in order to limit the exotherm. Preferably, the reaction proceeds adiabatically, with no removal of heat. When conducted adiabatically, the reaction conditions are preferably selected to control the maximum temperature to less than about 160° C., preferably from about 120 to about 150° C.

The generation of heat in the process provides a convenient basis for determining the optimum placement of the static mixing elements, particularly in an adiabatic process. As the reaction mixture travels through the coalescing zones of the tubular reactor, the acid and organic phases separate. At this point, the reaction rate slows dramatically, and little or no exotherm is produced. By measuring the temperature of the reaction mixture (or, preferably, the outside surface temperature of the tubular reactor) along the length of a coalescing zone, one can, for a specific set of reaction conditions, determine the point in the coalescing zone where the phase separation has occurred and the next static mixing element can be located. The optimum spacing of the static mixer elements can thus be determined empirically (or by appropriate modeling) for any set of reaction conditions.

For nitrations of aromatic compounds, the length of the coalescing zones will depend on several factors, including the particular aromatic compound being nitrated, the ratios of reactants, flow rates and the like. In these reactions, the nitrated product tends to act as a compatibilizer for the organic and acid phases. Consequently, as more nitrated product forms, the reaction mixture becomes more resistant to phase separation, and the time needed for phase separation to occur increases as the reaction progresses. Thus, longer coalescing zones may be needed in the downstream sections of the tubular reactor.

For many products of primary commercial significance, such as mononitrobenzene and dinitrotoluene, the time needed to achieve the necessary phase separation is at least about 1 second, preferably at least about 2 seconds, and more preferably at least about 3 seconds, near the beginning of the process, before large amounts of nitrated product are produced. Accordingly, the length of the coalescing zones near the beginning of the process are selected so as to provide residence times of at least 1 second, preferably at least 2 seconds and more preferably at least 3 seconds. As nitrated product builds up in the system, the time needed for phase separation to occur may rise to 5, 10 seconds, or even more. Thus, the length of the coalescing zones towards the middle or end of the process are advantageously chosen to provide a residence time of at least about 5 seconds, more preferably at least about 10 seconds. Another suitable variation is to provide coalescing zones of intermittently increasing length, so that residence times in the coalescing zone increase as the reaction mixture proceeds through the tubular reactor. Thus, for example, a tubular reactor can be provided in which the residence time in the first coalescing zone or zones is relatively short, say 1 to about 7 seconds, preferably 3–5 seconds, and residence times in succeeding coalescing zones increase gradually to 10 seconds or more.

Appropriate flow rates fall within the general limits mentioned before, i.e., from about 0.25 m/s, preferably about 0.5 m/s, to about 5 m/s, preferably to about 3 m/s, more preferably to about 1.5 m/s.

The reaction preferably goes substantially to completion, (i.e., 90% or more, more preferably 97% or more, even more preferably 98% or more, most preferably 98.5% or more) in the tubular reactor. Overall residence times and tubular reactor lengths within the general ranges described above are suitable for nitration reactions. The reaction mixture is then discharged from the outlet end of the tubular reactor to appropriate equipment for recovering the product from the acid phase. Spent sulfuric acid is preferably reconcentrated and recycled back into the process. In the preferred adiabatic process, the heat of nitration is available to be used in the acid reconcentration step.

Because of the corrosive nature of the reaction mixture, the tubular reactor and static mixing elements are made from a material that is resistant to corrosion in an acidic environment. For reaction in which the aromatic compound is used in excess, tantalum equipment, or equipment lined with glass or with a fluoropolymer stable at the service conditions, is suitable, for example equipment lined with a TEFLON (trademark of E. I. du Pont de Nemours and Company) industrial coating such as polytetrafluoroethylene, fluorinated ethylene propylene copolymer or perfluoroalkoxy non-stick coating. For reactions in which the nitric acid is used in excess, Teflon-lined carbon steel or stainless steel equipment is sufficient. Iron-silicium is a suitable material of construction for any necessary pumps for handling the acids.

This process provides several significant advantages. The short static mixing sections create small to moderate pressure drops. Consequently, standard sized, commercially available pumping equipment can often be used to build single-train, world-scale nitration plants, thereby decreasing the overall capital expense of the process. Energy consumption is correspondingly reduced.

The process also provides a crude product containing low levels of impurities. For benzene mononitration, dinitrobenzene levels are easily kept to below 300 ppm, often are below 200 ppm and can range from about 50–200 ppm even in commercial-scale facilities. These low dinitrobenzene levels are often accompanied by very high yields (98.5% or more of the nitric acid conversion to mononitrobenzene. Further, the crude product often contains below 2000 ppm, preferably below 1800 ppm, more preferably below 1650 ppm, especially below 1500 ppm nitrophenolic impurities. For benzene nitrations, the crude product often contains below 1000 ppm, preferably below 500 ppm, more preferably below 200 ppm of picric acid.

The following example is provided to illustrate the invention but is not intended to limit the scope thereof. All parts and percentages are by weight unless otherwise indicated.

EXAMPLE

A mixture of sulfuric acid and nitric acid containing 65.7% by weight of sulfuric acid, 4.0% by weight of nitric acid and 30.3% by weight of water is prepared by piping streams of sulfuric acid and nitric acid to a tee. Once steady-state conditions are achieved, the sulfuric acid is a recycle stream that is heated to about 95° C. The nitric acid stream is heated to about 60° C. before mixing with the sulfuric acid stream. The resulting acid mixture and a benzene stream are mixed at a weight ratio of approximately 18.5:1 (molar ratio benzene/nitric acid of 1.10:1) by pumping the mixture through a mixing plate corresponding to that shown in FIG. 2 located at the inlet of a tubular reactor. The flow rate is 98 cm/s. The tubular reactor contains 12 additional mixing plates (numbered 1–12, in order) separated by coalescing zones. In addition, a coalescing zone separates the plate used for mixing the acid and benzene streams and the plate numbered 1. Plate numbers 1 and 2 correspond to that shown in FIG. 2, and the remaining 10 plates correspond to that shown in FIG. 3. The lengths of the coalescing zones are such to provide the following residence times:

| Location of Coalescing Zone | Residence Time (sec) |
|---|---|
| Between initial acid/benzene mixing plate and plate 1 | 1.6 |
| Between plate 1 and plate 2 | 5.3 |
| Between plate 2 and plate 3 | 3.2 |
| Between plate 3 and plate 4 | 2.9 |
| Between plate 4 and plate 5 | 3.1 |
| Between plate 5 and plate 6 | 2.3 |
| Between plate 6 and plate 7 | 7.1 |
| Between plate 7 and plate 8 | 6.9 |
| Between plate 8 and plate 9 | 6.9 |
| Between plate 9 and plate 10 | 6.9 |
| Between plate 10 and plate 11 | 20.4 |
| Between plate 11 and plate 12 | 6.9 |
| Following plate 12 | 64.5 |

The coalescing zones are oriented generally horizontally. Because of the length of the coalescing zones, many of them contain elbows or bends.

The reaction proceeds adiabatically, with the exotherm raising the temperature of the reaction mixture. The temperature of the reaction mixture at the outlet is 135° C. Total residence time is about 138 seconds.

Yield of product is 98.8%. The crude product, before washing and finishing, contains 120 ppm dinitrobenzenes (3 isomers), 1200 ppm dinitrophenols, 1480 ppm total nitrophenolics, and 110 ppm picric acid.

What is claimed is:

1. A process for nitrating an aromatic compound, comprising passing under reaction conditions a reaction mixture including an aromatic compound and an acid phase containing sulfuric or phosphoric acid, nitric acid and water through a tubular reactor having a sequence of short static mixing elements separated by coalescing zones, wherein
   (a) the length of each of said coalescing zones is selected together with a flow rate of the reaction mixture such that as said reaction mixture passes through a coalescing zone, droplets of the aromatic compound coalesce and at least partially phase separate from said acid phase, forming a topmost portion of said reaction mixture rich in the organic compound and a bottommost portion of said reaction mixture poor in the organic compound, and
   (b) when said reaction mixture passes from a coalescing zone through a static mixer element, said topmost and bottommost portions are sheared and blended to redisperse the aromatic compound as small droplets in the acid phase and
   (c) at least one of said static mixing elements is a perforated plate oriented inside the tubular reactor substantially perpendicularly to the direction of flow of said reaction mixture and the perforated plate contains perforations over only a topmost or bottommost portion of its surface.

2. The process of claim 1, wherein the residence time of the reaction mixture in each of the static mixing elements is less than 1 seconds.

3. The process of claim 2, wherein the residence time of the reaction mixture in each of the coalescing zones is at least about 1 seconds.

4. The process of claim 1, wherein the length of the coalescing zones increases towards the outlet end of the reactor.

5. The process of claim 1, wherein the length of the coalescing zones decreases towards the outlet end of the reactor.

6. The process of claim 1, wherein the reaction mixture flows through the tubular reactor at a rate of about 0.25–5 meters/second.

7. The process of claim 1, wherein the aromatic compound is benzene, the acid phase contains about 62–68% sulfuric acid, 2.5–6% nitric acid and 28–35% water, and the molar ratio of benzene to nitric acid is about 1.05 to about 1.15:1.

8. The process of claim 7 including a step of recovering a stream of crude mononitrobenzene from the tubular reactor in a yield of at least 98.5%, the crude mononitrobenzene containing, before washing and finishing, less than 200 ppm dinitrobenzene isomers, less than 1650 ppm nitrophenolic impurities, and less than 500 ppm picric acid.

9. The process of claim 1, wherein the aromatic compound is toluene, the acid phase contains sulfuric acid, nitric acid and water, and the molar ratio of toluene to nitric acid is about 0.4 to about 0.55:1.

10. The process of claim 1, wherein the reactor comprises coalescing zones oriented generally horizontally to facilitate gravimetric phase separation, and gravimetric phase separation occurs in the coalescing zones.

11. The process of claim 1, wherein the reactor contains at least 5 static mixing elements.

12. The process of claim 1, wherein the pressure drop across each static mixing elements is no greater than about 0.7 bar, at the flow rates used in the process.

13. The process of claim 2, wherein each static mixing element has a length/diameter ratio of no greater than about 0.5 and wherein the operating flow rate are such that the residence time of the reaction mixture in each static mixing element is no greater than about 0.25 second.

14. The process of claim 13, wherein
   (a) the reactor contains at least 7 to about 25 perforated plates, each containing perforations over bottommost portion of its surface including at least one perforation near the bottom to facilitate draining the tubular reactor,
   (b) the residence time of the reaction mixture in each of the coalescing zones is at least about 1 second,
   (c) the length of the coalescing zones increases toward the outlet end of the reactor,
   (d) the reaction mixture flows through the tubular reactor at a rate of about 0.25–5 meters/second,
   (e) the pressure drop across each static mixing element is no greater than about 0.7 bar,
   (f) the aromatic compound is benzene, the acid phase contains, by weight, about 62–68% sulfuric acid, 2.5–6% nitric acid and 28–35% water, and the molar ratio of benzene to nitric acid is about 1.05:1 to about 1.15:1, and
   (g) the process includes a step of recovering a stream of crude mononitrobenzene containing, before washing and finishing, less than 200 ppm dinitrobenzene isomers, less than 1650 ppm nitrophenolic impurities, and less than 500 ppm picric acid.

* * * * *